United States Patent

Prasad et al.

[11] Patent Number: 5,330,441
[45] Date of Patent: Jul. 19, 1994

[54] SURGICAL SUTURING NEEDLE AND METHOD FOR MAKING SAME

[75] Inventors: Janniah S. Prasad; Robert Maurer; Paul Kapralos, all of Fairfield, Conn.; John E. Buzerak, Dutchess, N.Y.; Charles L. Putnam, Belle Mead, N.J.

[73] Assignee: American Cyanamid Company, Wayne, N.J.

[21] Appl. No.: 55,165

[22] Filed: Apr. 30, 1993

[51] Int. Cl.⁵ .................................. A61B 17/00
[52] U.S. Cl. ........................... 606/222; 606/223; 165/1; 165/5
[58] Field of Search ................ 606/222–227; 163/1, 5; 223/102

[56] References Cited

U.S. PATENT DOCUMENTS

| | | | |
|---|---|---|---|
| 3,160,157 | 12/1964 | Chisman | 606/223 |
| 4,513,747 | 4/1985 | Smith | 606/223 |
| 4,799,484 | 1/1989 | Smith et al. | 606/223 |
| 5,030,228 | 7/1991 | Wong et al. | 606/222 |
| 5,178,628 | 1/1993 | Otsuka et al. | 163/5 |
| 5,263,974 | 11/1993 | Matsutani et al. | 606/223 |

Primary Examiner—Stephen C. Pellegrino
Assistant Examiner—Gary Jackson
Attorney, Agent, or Firm—Charles F. Costello, Jr.

[57] ABSTRACT

A surgical suturing needle is formed to have a needle shaft with a rectangular cross-section and a needle head with a triangular needle point. A transitional portion between the needle shaft and the needle head is formed to have a maximum width greater than the width of the needle shaft. A plurality of cutting edges extend from the needle point to at least the maximum width section of the transitional portion. After forming and grinding the suturing needle, it is immersed in an acid bath and exposed to an electrical field. Finally, the surgical needle is heat-treated to increase its strength and resistance to bending or breaking.

26 Claims, 3 Drawing Sheets

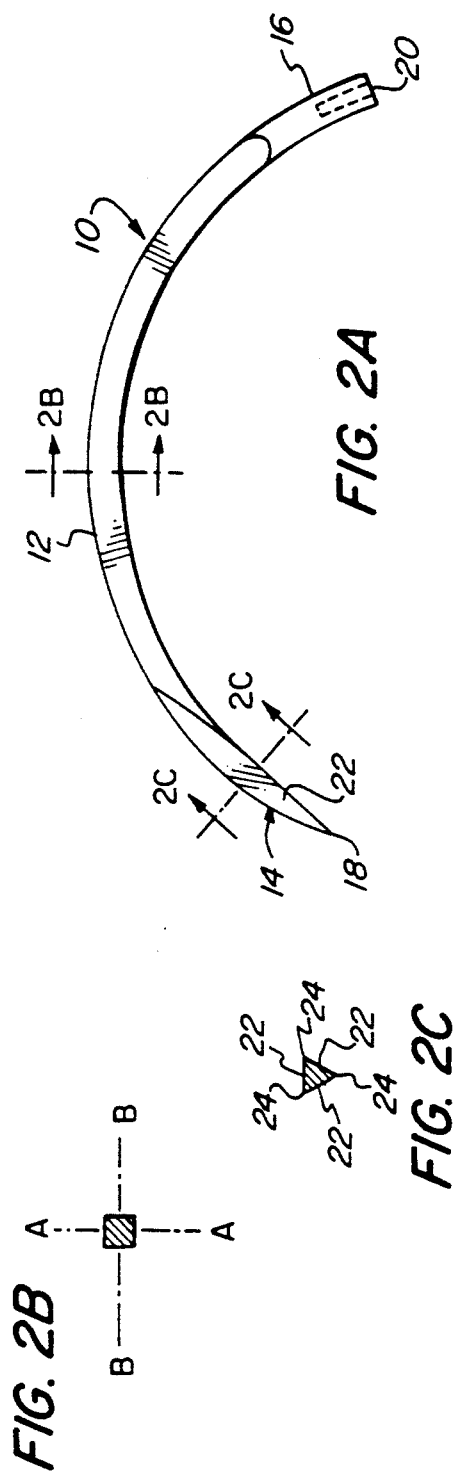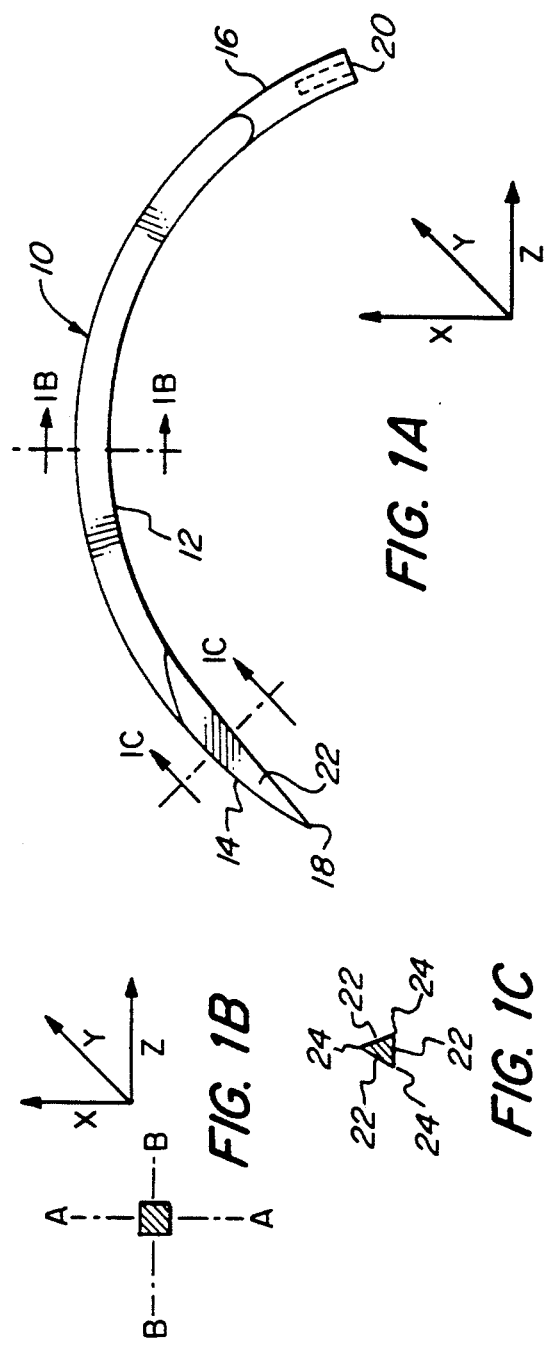

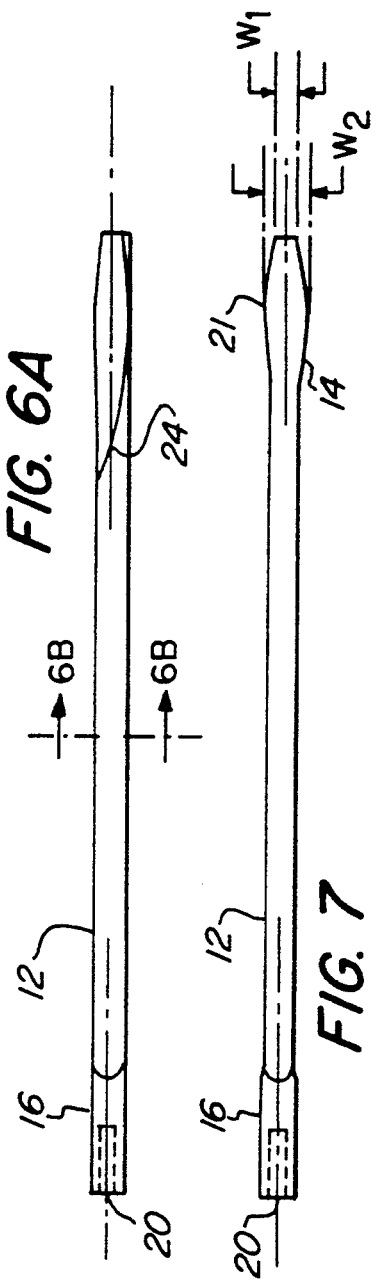

FIG. 8

| NEEDLE TYPE | NEEDLE GEOMETRY | | | NEEDLE PERFORMANCE | | | |
|---|---|---|---|---|---|---|---|
| | SOURCE | LENGTH, mm | RADIUS OF CURVATURE, mm | INCLUDED ANGLE | PENETRATION FORCE, gm[1] | STRENGTH,[2] SPAN, cm / MOMENT TO BEND, cm gm 30° / 90° | DUCTILITY[3] |
| XPRE-1 | D&G | 11 | 5 | 130° | 30 | 0.64  134  163 | 23 |
| PRE-1 | SULZLE | | | | 68 | 0.64  84  114 | 4 |
| P-1 | ETHICON | | | | 53 | 0.64  91  139 | 4 |
| XPRE-2 | D&G | 13 | 5 | 150° | 41 | 0.80  492  544 | 6 |
| PRE-2 | SULZLE | | | | 91 | 0.80  207  268 | 3 |
| P-3 | ETHICON | | | | 61 | 0.80  190  225 | 3 |
| XPRE-4 | D&G | 19 | 8 | 135° | 59 | 1.11  933  1037 | 6 |
| PRE-4 | SULZLE | | | | 79 | 1.11  328  449 | 1 |
| PS-2 | ETHICON | | | | 77 | 1.11  449  639 | 4 |
| XPRE-6 | D&G | 24 | 10 | 135° | 48 | 1.43  985  1261 | 10 |
| PRE-6 | SULZLE | | | | 114 | 1.43  605  933 | 2 |
| PS-1 | ETHICON | | | | 83 | 1.43  795  1054 | 7 |

NOTES:
1. AVERAGE OF 10 NEEDLES PER LOT, 3 PENETRATIONS PER NEEDLE THROUGH RABBIT SKIN. LOWER THE FORCE, SHARPER THE NEEDLE.
2. AVERAGE OF 10 NEEDLES PER LOT. TESTED IN TINIUS-OLSEN TESTER
3. AVERAGE OF 10 NEEDLES PER LOT. MANUAL BENDING THROUGH 30° ON EITHER SIDE OF THE NOMINAL POSITION.

SURGICAL SUTURING NEEDLE AND METHOD FOR MAKING SAME

BACKGROUND OF THE INVENTION

1. Field of the Invention

The present invention relates to a design and method of manufacturing a surgical suturing needle that can be used generally for adjoining or closing adjacent portions of skin or tissue. More particularly, the suturing needle design and manufacturing process of the present invention are directed to a new class of suturing needle particularly suitable in plastic and reconstructive suturing applications.

2. Description of the Prior Art

Suturing needles for applying sutures, or stitches, by hand in cutaneous and subcutaneous tissues are well known in the art. The sutures are typically used to close wounds or adjoin adjacent tissue, often at the conclusion of a surgical procedure. Conventional suturing needles are usually made from a cut blank of material such as stainless steel. The cut blank is metal-worked using well known machining techniques to form a surgical suturing needle. The needle generally includes a shaft, a rear end portion with means to grip or secure a suturing thread and a needle head at a front end portion for puncturing skin and tissue through which the needle travels. The needle head typically includes a sharpened needle tip at its distal end and cutting edges.

Needle sharpness is an important consideration in designing and manufacturing surgical suturing needles. Sharper needles require less force to penetrate the tissue and thus cause less tissue trauma. In addition, sharper needles reduce fatigue on the needle itself, making it less likely to bend or break during suturing. Needle sharpness is typically defined in terms of a so-called penetration force -- the force necessary for a needle point to puncture, or penetrate, the tissue. The penetration force is primarily determined by the design and sharpness of the needle point. However, needle sharpness is also affected by a drag force of the needle as it travels through the tissue. The ability of the needle to pass smoothly through the tissue is a desirable characteristic. The drag force of the needle depends upon the design and sharpness of the needle, especially the needle head. The quality of a lubricating coating on the needle also affects the drag force. For example, if the lubricating coating on the needle wears off, the drag force on the needle increases with each pass of the needle through the tissue. This effect could give the surgeon-user the false impression that the needle is failing to retain its sharpness.

Another important consideration in designing and manufacturing surgical suturing needles is their resistance to bending or breaking during use. The strength of a suturing needle is a measure of its ability to resist bending and is determined by such factors as (a) the material selected to make the needle, (b) the cross-sectional shape of the needle, and (c) the heat treatment process received by the needle during manufacturing. However, needle strength should be balanced by needle ductility, which is defined in terms of the ability of the needle to be reshaped after it flexes from its original shape. A surgical needle with good strength characteristics but having little or no ductility can be brittle and may snap and break during use. In use, the surgical needle is held at its rear end by a needle holder and the needle tip is forced against the tissue to be sutured. This action creates a bending moment on the needle body, and a needle with some degree of ductility will be able to be reshaped to its original shape without breaking. It is generally known that in working with a metallic material, as the strength of the material increases the ductility will decrease. Therefore, it is desirable to carefully balance the strength and ductility characteristics of a suturing needle.

Another desirable attribute is stability of the suturing needle in a needle holder. The needle holder is typically used to grip and stabilize the needle as it passes through the tissue.

The subject invention provides significant advances over conventional surgical suturing needles by improving needle attributes such as needle sharpness and resistance to bending or breaking during use as well as other desirable attributes.

SUMMARY OF THE INVENTION

Accordingly, it is a general object of the present invention to provide an improved surgical suturing needle and a method for making such needles.

It is another object of the present invention to provide a surgical suturing needle with superior resistance to bending and breaking during use.

It is yet another object of the present invention to provide a surgical suturing needle with superior ability to easily penetrate the skin or tissue.

It is still another object of the present invention to provide a surgical suturing needle designed to reduce drag force as it travels through the skin and tissue.

It is another object of the present invention to select materials for the surgical suturing needle that will improve its resistance to bending and breaking and increase the ease with which it penetrates and travels through skin and tissue.

It is still another object of the present invention to provide a surgical suturing needle design that will improve its resistance to bending or breaking and increase the ease with which it penetrates and travels through skin and tissue.

It is another object of the present invention to provide a surgical suturing needle manufacturing process that will improve the resistance of the needle to bending and breaking and increase the ease with which it penetrates and travels through skin and tissue.

These objects are achieved by the present invention, which in a preferred embodiment is surgical suturing needle that comprises a needle shaft having a rectangular cross-section, and a multi-sided needle head having a needle point with a plurality of cutting edges extending axially from the needle head and defining sides of the needle head. A transitional portion adjoins the needle shaft and the needle head and has a maximum width greater than the width of the needle shaft. This design may be called "cobra-headed."

The method of manufacturing a surgical suturing needle in accordance with a preferred embodiment of the present invention comprises the step of metal-working a needle blank to form a shaft portion, having a rectangular cross-section, that terminates in a needle point and having a plurality of cutting edges. The needle head is then worked to form a transition portion between the shaft portion and the needle head that has a width greater than the width of the shaft portion. The cutting edges extend axially from the needle point at least to this transition portion. Finally the needle point and cutting edges are sharpened.

These and other objects, aspects, features and advantages of the present invention will become apparent from the following detailed description of the preferred embodiments taken in conjunction with the accompanying drawings.

BRIEF DESCRIPTION OF THE DRAWINGS

FIG. 1A is a plan view of a surgical suturing needle of the present invention;

FIG. 1B is a cross-sectional view taken at plane 1B—1B of the surgical suturing needle illustrated in FIG. 1A;

FIG. 1C is a cross-sectional view taken at plane 1C—1C of the surgical suturing needle illustrated in FIG. 1A;

FIG. 2A is a plan view of the surgical suturing needle of the present invention;

FIG. 2B is a cross-sectional view taken at plane 2B—2B of the surgical suturing needle illustrated in FIG. 2A;

FIG. 2C is a cross-sectional view taken at plane 2C—2C of the surgical suturing needle illustrated in FIG. 2A;

FIG. 3 is an elevational view of the surgical suturing needle of the present invention;

FIG. 4 is a plan view of the surgical suturing needle of the present invention;

FIG. 5A is an elevational view of a cut blank used to form the surgical suturing needle of the present invention;

FIG. 5B is a cross-sectional view taken at plane 5B—5B of the cut blank illustrated in FIG. 5A;

FIG. 6A is an elevational view of a coined preform used to form the surgical suturing needle of the present invention;

FIG. 6B is a cross-sectional view taken at plane 6B—6B of the coined preform illustrated in FIG. 6A;

FIG. 7 is a front elevational view of a coined preform used to form the surgical suturing needle of the present invention; and FIG. 8 is a table showing comparable data between a surgical suturing needle of the subject invention and two conventional needles.

DESCRIPTION OF THE PREFERRED EMBODIMENTS

The surgical suturing needle of the present invention is designed and manufactured to possess attributes of primary importance in suturing needles. For example, the suturing needle of the present invention is designed with superior needle sharpness to penetrate and travel easily through the cutaneous and subcutaneous layers of tissue. The surgical needle of the subject invention also has superior strength and resistance to bending and/or breaking during use.

In achieving these desirable characteristics, a threefold approach is used to produce the surgical suturing needle of the subject invention. As discussed below, each component of this three-fold approach is interdependent, and is preferably used in conjunction with the other components to achieve an optimum suturing needle. The first component is proper selection of the material for the surgical needle to obtain superior physical characteristics. Second, the needle is designed in a way to enhance its penetration characteristic and the ability to travel through the tissue and to provide it with superior physical characteristics, and third, particular manufacturing steps are used in metal-working the needle to achieve optimum benefits of the needle design.

The choice of materials is of primary importance to the physical characteristics, that is, strength, ductility and resistance to bending or breaking of the needle. However, the cross-sectional shape and dimensions of the needle and the heat-treating process which the needle receives during the manufacturing process also contribute to the physical characteristics of the needle. The suturing needle of the present invention is preferably made from AISI 302 type stainless steel. However, AISI types 301 or 304, which possess similar characteristics to AISI 302, can also be used. These '300' series stainless steels, which typically have a tensile strength of between 325,000–350,000 lbs/in$^2$, attain their high strength from undergoing cold working as the material is converted from an ingot to wire of the desired diameter.

The design of the surgical needle of the present invention contributes to both its strength and resistance to bending and to its ability to easily pierce and travel through the tissue to be sutured. The finished needle 10 is shown in FIG. 1A to have a curved needle shaft 12 with a needle head 14 at its distal end and a rear end portion 16 at its proximal end. The needle head 14 terminates in a needle point 18 for piercing the skin or tissue. The rear end portion 16 includes an axial hole 20 for receiving and securing a suturing thread. Of course, other means for securing the suturing thread within the proximal end of the needle shaft, such as for example, a crimping channel, are also contemplated.

In accordance with the subject invention, the cross-sectional area of the needle shaft 12 is rectangular in shape as shown in FIG. 1B. While conventional needles typically have cross-sections that are round or triangular, the rectangular cross-section of the present invention provides strength superior to that of conventional cross-sections over the same area. The major axis A—A of the rectangular cross-section is in the plane of curvature, i.e, the X-Y plane, of the needle and the minor axis B—B lies in the X-Z plane (as seen in FIGS. 1A and 2A). Although an excessively pronounced rectangular shape can further increase the strength of the needle, such a cross-sectional shape reduces the stability of the needle in a needle holder. Therefore, it is preferable to shape the rectangular cross-section to have a major axis to minor axis ratio of 1.2 or less.

As best seen in FIGS. 3 and 4, the needle head 14 is shaped to have three sides 22 tapering toward the distal end of the needle to form the needle point 18. The cross-section of the needle point is triangular in shape as shown in FIGS. 1C and 2C, and the three corners of the triangle, that is, the edges adjoining each adjacent side 22, form cutting edges 24 for slicing the cutaneous and subcutaneous tissue. The included angle A of the needle point is preferably between 25° and 29° as shown in FIG. 3. A smaller included angle would reduce the necessary penetration force but would also increase the susceptibility of the needle point to damage during fabrication or use. On the other hand, a larger included angle increases the durability of the needle point but also requires an undesirable increase in force necessary to penetrate the cutaneous tissue.

The needle head 14 of the subject invention also features a cobra head shape, wherein the widest portion of the needle head has a width $W_2$ slightly greater than the width $W_1$ of the needle shaft as shown in FIG. 3. The widest portion of the needle head 14 is identified as transition portion 21 in FIGS. 3, 4 and 7. Moreover, the cutting edges 24 extend from the needle point 18 to at least the widest part of the needle head 14. In this manner, the three cutting edges 24 slice the tissue as the needle head passes therethrough and provide an opening slightly larger than the shaft 12 of the needle, thus significantly reducing the drag force, and allowing the shaft to pass easily through the tissue. The length of the cutting edges are preferably between 3 and 7 times the diameter of the wire, or cut blank, used for the needle.

The manufacturing process of the subject invention begins with selection of a cut blank from a coil of wire made of one of the preferred materials discussed above. The cut blank 26 is shown in FIG. 5A, and has a conventional round cross-section 27 as shown in FIG. 5B. The cut blank is worked with a conventional press or swaging machine to form the needle shaft 12 with a rectangular cross-section 13 as shown in FIGS. 6A and 6B. As shown in FIGS. 6A and 7, the proximal end 16 of the needle shaft can retain its circular cross-section, and is machined to provide an axial hole 16, or other comparable means, for securing the suturing thread to the needle.

After the shaft is formed, the three-sided needle head 14 is formed at the distal end by using, for example, a three-jaw toggle press or a swaging machine. The three sides 22 are first worked to form a blunt end "cobra-head" type shape with transition portion 21 having a maximum width $W_2$ slightly larger than the width $W_1$ of the needle shaft 12 as described above. The cutting edges 24 will also necessarily be curved as shown in FIG. 6A, as the three-sided needle head 14 meets with the four-sided needle shaft 12. A coined preform of the suturing needle is thus formed at the manufacturing stage shown in FIGS. 6A and 7.

Progressively finer grinding media, such as an abrasive belt, are then used to finish shaping the cobra head and form a needle point 18 at the distal end of the needle head. The needle point and cutting edges are further honed to form sharp cutting edges. The use of progressively finer sharpening media minimizes any burr formation on the cutting edges of the needle head.

The surgical needle is then curved to its appropriate shape at this stage of the manufacturing process by conventional means, making sure the major axis of the rectangular cross-section is in the plane of curvature of the needle as described above with reference to FIGS. 1A, 1B, 2A, and 2B. As will be appreciated, the particular radius of curvature of the needle is a matter of design application and user preference. Of course, a straight needle design can be used without departing from the scope of the invention.

The surgical needle is then exposed to an electrical field while being immersed in an acid bath. This electrochemically processing step removes any burrs left from the grinding process and smooths without dulling the cutting edges of the needle head. While the actual amount of material removed in this step is very small, electrohoning can reduce by 30% to 40% the force necessary to penetrate the tissue. The time of exposure, temperature of the acid bath and the current density of the electrical field should be carefully controlled to obtain the maximum benefit of this step. For example, when using AISI 302 type stainless steel as the material for the needle, the temperature of the acid bath is preferably within a range of 130° to 180° F., and more preferably around 150° F., the time of exposure can range from 3 to 20 minutes, with 8½ minutes found to be the optimum exposure time, and the preferred current density is 40 amps/ft$^2$, although a broader range of between 10 and 80 amps/ft$^2$ can be used depending upon the temperature of the acid bath and the time of exposure.

The metal-worked, fully shaped needle is then heat treated to increase its strength and resistance to bending. In the heat treating step, the needles are exposed to a temperature between 700° and 1100° F., and preferably between 800° and 900° F., for a time period of between 1 to 4 hours.

The heat treated needles can then be coated with a lubricant to enhance passage of the needle through the tissue. Conventional solutions for this purpose include silicones and Teflon ®.

As will be appreciated, the surgical suturing needle design of the subject invention is preferably made by the disclosed needle manufacturing process. However, the benefits of the needle design of the subject invention can be realized even if the needle is made by conventional manufacturing techniques.

Each component of the three-fold approach describe above, that is, material selection, needle design and the manufacturing process, are interdependent. Recognizing the interdependency of these components produces a superior surgical suturing needle that provides optimum performance.

FIG. 8 shows a table illustrating the comparative results of four groups of different sized needles. Each group contains a suturing needle made in accordance with the subject invention, identified by source as "D+G", and two conventional models. The first conventional needle in each group is marketed by Sulze ® and is shaped to have a three-sided needle head design and a body shape with a triangular cross-section. The second conventional needle in each group is marketed by Ethicon ® and has a three-sided needle head design and a round body shape with flattened top and bottom portions. Some of the Ethicon ® needles also have a 'cobra-head' type head design.

As the table shows, the first measurement of needle performance, penetration force, is lowest in each group for the needles made in accordance with the subject invention. The penetration force was measured using an average of 10 needles per lot, with three penetrations per needle through rabbit skin. As will be appreciated, lower penetration force is desirable, as this indicates superior needle sharpness and reduces tissue trauma. The second measurement of needle performance is strength as measured in a moment force needed to bend the needle. This test was performed using a Tinius-Olsen Tester with an average of 10 needles per lot. As the table in FIG. 8 illustrates, the 'D+G' needles required a greater moment force to bend the needles. Lastly, ductility was measured in the number of times a needle could be manually bent through 30° on either side of a nominal position without breaking. Again, an average of 10 needles per lot were tested. The needles of the subject invention demonstrated superior ductility over conventional needles by withstanding a greater number of bends before breaking.

Although a specific embodiment of the present invention has been described above in detail, it will be understood that this description is merely for purposes of illustration. Various modifications of and equivalent structures corresponding to the disclosed aspects of the preferred embodiment in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A method of making a surgical suturing needle from a blank, comprising the steps of:
    metal-working the blank to form a shaft portion of the needle with a rectangular cross-section, with said rectangular cross-section having a major axis and a minor axis and a ratio of the major axis to the minor axis of no more than about 1.2;
    metal-working a first end of the blank to form a needle head triangularly-shaped in cross-section terminating in a needle point and having a plurality of cutting edges;
    metal-working the needle head to form a transition portion between the shaft portion and the needle point with a width greater than a width of the shaft portion, with the cutting edges extending axially from the needle point to at least the transitional portion; and
    sharpening the needle point and cutting edges.

2. A method of making a surgical suturing needle according to claim 1, wherein said needle point has an included angle of between 25° and 29°.

3. A method of making a surgical suturing needle according to claim 1, further comprising the step of forming the cutting edges to have a length of 3 to 7 times a diameter of the blank.

4. A method of making a surgical suturing needle according to claim 1, further comprising the step of bending the suturing needle to form a curved needle.

5. A method of making a surgical suturing needle according to claim 1, further comprising the step of electrochemically processing the needle by placing it in an acid bath while exposing it to an electrical field.

6. A method of making a surgical suturing needle according to claim 1, further comprising the step of heat treating the curved needle.

7. A method of making a surgical suturing needle according to claim 6, wherein the heat treating step heats the needle to a temperature between 700° and 1100° F.

8. A method of making a surgical suturing needle according to claim 1, further comprising the step of lubricating the needle.

9. A method of making a surgical suturing needle according to claim 1, further comprising the step of metal-working a second end of the blank to form an axial opening for receiving a suturing thread.

10. A method of making a surgical suturing needle according to claim 1, wherein the sharpening step includes the step of grinding the needle head with progressively finer grinding media.

11. A method of making a surgical suturing needle from a blank, comprising the steps of:
    selecting a needle blank made of 300 series stainless steel;
    working the needle blank to form a shaft portion with a rectangular cross-section and a first width, with said cross-section having a major axis and minor axis and a ratio of the major axis to the minor axis of no more than about 1.2;
    shaping a first end of the needle blank to form a three-sided needle head terminating in a needle point having a plurality of cutting edges;
    sharpening the needle point and cutting edges;
    electrochemically processing the needle point and cutting edges; and
    heat treating the needle.

12. A method of making a surgical suturing needle according to claim 11, further comprising the step of applying a lubricating coating to the needle.

13. A method of making a surgical suturing needle according to claim 11, further comprising the step of metal-working a second end of the blank to form an axial opening for receiving a suturing thread.

14. A method of making a surgical suturing needle according to claim 11, wherein the sharpening step includes the step of grinding the needle head with progressively finer grinding media.

15. A method of making a surgical suturing needle according to claim 11, wherein the electrohoning step includes the step of placing the needle in an acid bath and exposing it to an electrical field.

16. A method of making a surgical suturing needle according to claim 11, wherein the heat treating step heats the needle to a temperature between 700° and 1100° F.

17. A method of making a surgical suturing needle according to claim 11, further comprising the step of bending the surgical needle to form a curved needle, wherein the heat treating step is done after the curved needle is formed.

18. A method of making a surgical suturing needle according to claim 11, further comprising the step of forming a transition portion on the needle head having a second width greater than the first width of the shaft portion.

19. A method of making a surgical suturing needle according to claim 11, further comprising the step of forming the cutting edges to have a length of 3 to 7 times a diameter of the blank.

20. A surgical suturing needle comprising:
    a needle shaft having a width and a rectangular cross-section with a major axis and a minor axis having a ratio of no more than about 1.2;
    a multi-sided needle head having a needle point with an included angle of between 25° to 29° and a plurality of cutting edges extending axially from said needle point and defining sides of said needle head; and
    a transitional portion adjoining said needle shaft and said needle head, with said transitional portion having a maximum width greater than the width of said needle shaft.

21. A surgical suturing needle according to claim 20, wherein said needle head has a three-sided configuration and a triangular cross-section.

22. A surgical suturing needle according to claim 20, wherein said cutting edges extend axially from said needle point and continue to at least said transitional portion.

23. A surgical suturing needle according to claim 22, wherein said cutting edges have a length from said needle point to the maximum width of said transitional portion of preferably 3 to 7 times a diameter of a metal wire used to form the surgical needle.

24. A surgical suturing needle according to claim 20, wherein an end of said needle shaft opposite to said needle head includes means for securing a suturing thread thereto.

25. A surgical suturing needle according to claim 20, wherein said suturing needle is made of 300 series stainless steel.

26. A method of forming a surgical needle head on a needle shaft, comprising the steps of:
  metal-working one end of the needle shaft to form a three-sided needle head terminating in a needle point, with the needle head having a plurality of cutting edges and a triangular cross-section; and
  forming a transitional portion on the needle head between the needle point and the needle shaft, with the transitional portion having a width larger than a width of the needle shaft, wherein
  the cutting edges extend axially from the needle point to at least the transitional portion of the needle head.

* * * * *